United States Patent [19]

Lauer

[11] 4,077,861

[45] Mar. 7, 1978

[54] POLAROGRAPHIC SENSOR

[75] Inventor: Jay M. Lauer, Hacienda Heights, Calif.

[73] Assignee: Teledyne Industries, Inc., San Gabriel, Calif.

[21] Appl. No.: 739,253

[22] Filed: Nov. 5, 1976

Related U.S. Application Data

[62] Division of Ser. No. 653,017, Jan. 28, 1976, abandoned.

[51] Int. Cl.² ............................................ G01N 27/46
[52] U.S. Cl. .................. 204/195 P; 128/2 E; 204/1 T; 324/29
[58] Field of Search ............... 204/195 P, 1 P, 195 R, 204/1 T; 324/29; 128/2 E, 2.1 E

[56] References Cited

U.S. PATENT DOCUMENTS

| | | | |
|---|---|---|---|
| 2,805,191 | 9/1957 | Hersch | 204/1 T |
| 2,898,282 | 8/1959 | Flook et al. | 204/195 R |
| 3,334,039 | 8/1967 | Vlasak | 204/195 P |
| 3,503,861 | 3/1970 | Volpe | 204/195 P |
| 3,718,563 | 2/1973 | Krull et al. | 204/195 P |
| 3,838,034 | 9/1974 | Groves | 204/195 P X |

*Primary Examiner*—G. L. Kaplan
*Attorney, Agent, or Firm*—Marvin E. Jacobs

[57] ABSTRACT

An apparatus and method for polarographically determining the amount of oxygen in a gaseous mixture containing interfering reducible gases such as nitrous oxide is disclosed. The invention has particular application to the determination of oxygen in nitrous oxide containing anesthetic gas mixtures. The oxygen content is determined by operating a special polarographic cell at about −0.6 volts, which is below the voltage at which nitrous oxide would be sensed polarographically. A special cathode is utilized in which the exposed cathode face is disposed near the periphery of a cathode support mounted centrally under the gas permeable membrane so that ion mobility is increased to decrease the internal resistance of the electrochemical cell. It is also found that at the low operating voltage the cathode tends to become passivated or inactive after use. In accordance with the invention the cathode is activated at turn-on by reversing polarity and applying a positive voltage pulse to the cell.

10 Claims, 4 Drawing Figures

U.S. Patent
March 7, 1978
4,077,861
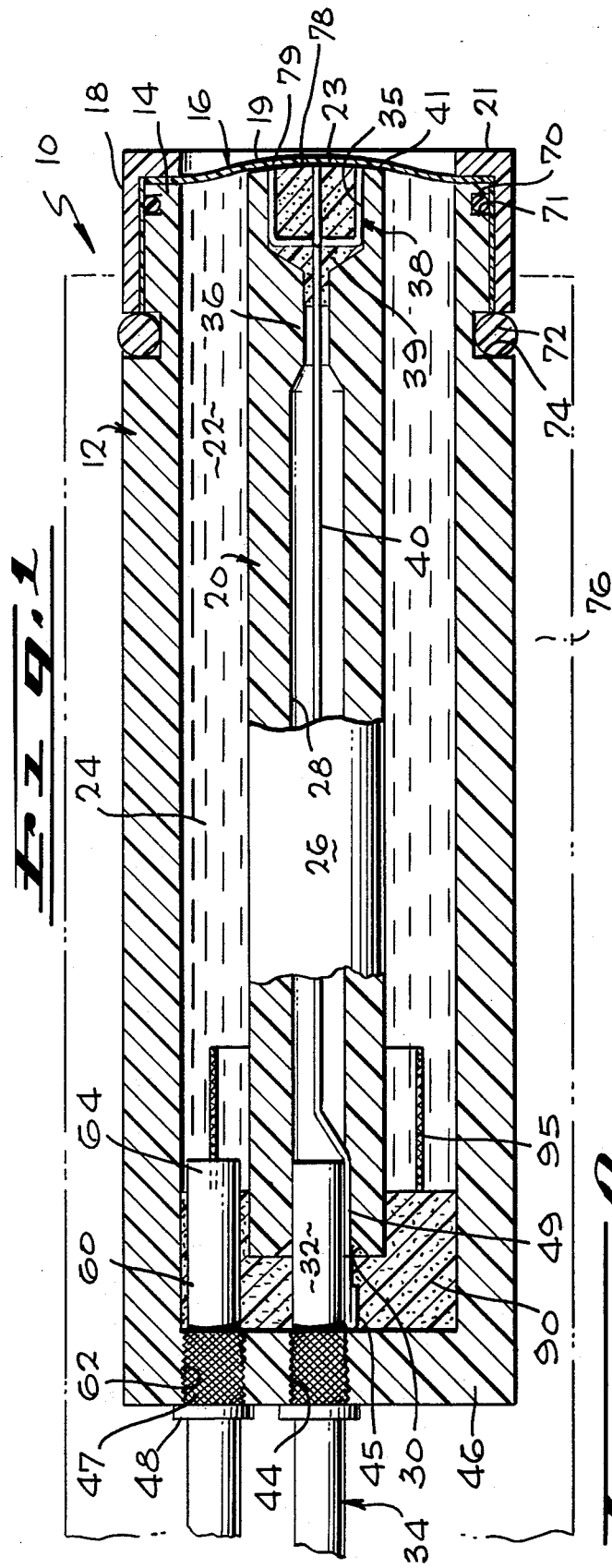
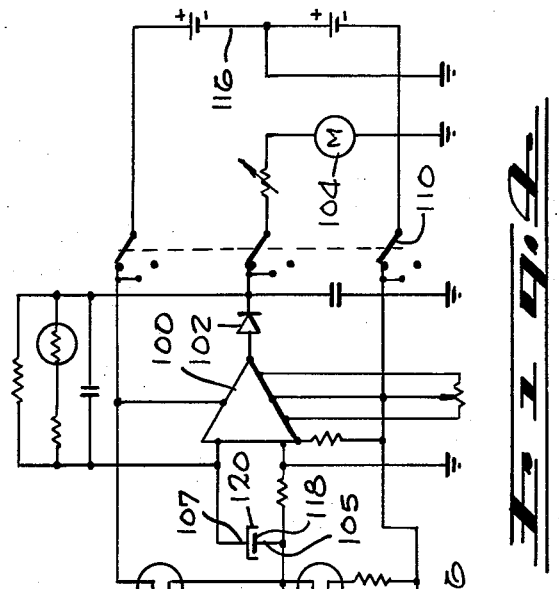
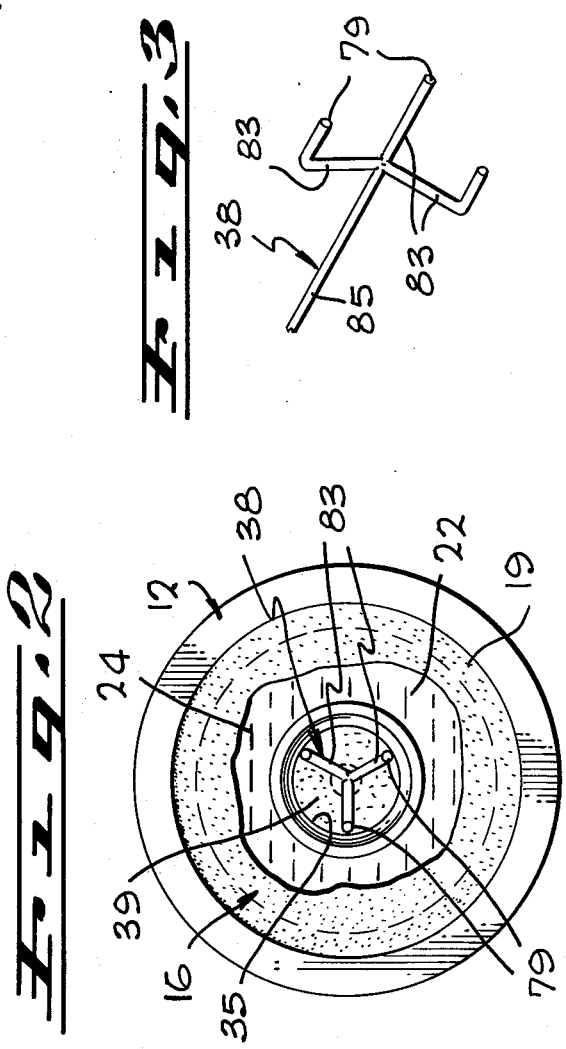

POLAROGRAPHIC SENSOR

CROSS REFERENCE TO RELATED APPLICATION

This application is a division of Ser. No. 653,017, filed Jan. 28, 1976 and now abandoned.

BACKGROUND OF THE INVENTION

1. FIELD OF THE INVENTION

The present invention relates to an electrochemical polarographic gas analyzer and, more particularly, to a gaseous phase oxygen analyzer and to methods of using the analyzer to determine oxygen in the presence of other gases having polarographic reduction potentials near to that of oxygen.

2. DESCRIPTION OF THE PRIOR ART

Electrochemical gas analyzers have been available for several years which measure oxygen content of a gas or fluid by diffusing oxygen through a semi-permeable membrane into an electrolyte layer adjacent the cathode. A polarographic voltage is applied relative to an anode spaced therefrom and the resultant depolarizing current is measured by means of an external circuit.

The linearity and accuracy of response and the magnitude of the electrical signal are affected by the spacing of the membrane from the cathode and by the cathode response characteristics. A further limitation in the life of the electrochemical cell is the electrolyte. Typical electrolytes for polarographic sensors are aqueous solutions of alkali metal halides which tend to dry out as the cell is used, requiring the cell to be discarded unless it is of the type in which the electrolyte may be replaced. Opening the cell to replace electrolyte is a difficult operation, especially in the field, and cells with replaceable electrolyte require purchase and storage of the electrolyte and replacement membranes.

One application in which oxygen sensing electrochemical cells have been utilized is in the determination of the oxygen content of clinical, anesthetic nitrous oxide containing gas mixtures. One type of cell utilized currently is a galvanic cell. However, during operating the anode employed, which reduces oxygen at the cathode, will also reduce nitrous oxide to nitrogen at its surface. The nitrogen produced at the anode collects within the sealed electrochemical cell, causing lifting of the membrane, which changes the thickness of the electrolyte film and therefore the diffusion path from membrane to cathode causing incorrect readings and may eventually lead to rupture of the gas permeable membrane.

SUMMARY OF THE INVENTION

An improved electrochemical polarographic system for analyzing oxygen content in the gaseous phase has been provided in accordance with the invention. The oxygen content of an anesthesia gas mixture is sensed in accordance with the invention by means of a polarographic cell in which the polarizing voltage is set to be no higher than about −0.6 volts, and in which the cathode is so configured that ion mobility is very high. Tailing signals are avoided providing rapid response, precision, accuracy and linearity. The electrochemical polarographic cell is in the form of a sealed disposable module having long service life expectancy and low replacement cost.

The cell exhibits an ultrafast response of 90% in less than 5 seconds and being disposable, there is no electrolyte nor membrane to change. The cell includes a relatively large body of electrolyte which does not dry out during the normal interval of use. The life expectancy of the cell is three to six months in average anesthesia applications. The cell is completely unaffected by nitrous oxide and accurate readings can be obtained even in wet, condensing environments. The invention also relates to special activation procedures that may be required to activate the cathode which becomes passivated when stored in an unpolarized state and subsequently operated in this very low voltage mode.

The greater portion of the electrode surface area is near the outer edge of the face of the cathode. Since the electrolyte is fed by capillary action, the resistance of motion of ions is less near the edge and the response is better since the electrochemical resistance is lower. Speed of response is better and the response characteristics are more linear with the cell configuration of this invention.

These and many other features and attendant advantages of the invention will be readily appreciated as the invention becomes better understood by reference to the following detailed description when considered in conjunction with the accompanying drawings.

BRIEF DESCRIPTION OF THE DRAWINGS

FIG. 1 is a side elevational view partially broken away in section of the electrochemical cell module of the invention;

FIG. 2 is a front elevational view partially in section of the cell module of FIG. 1;

FIG. 3 is a perspective view of the cathode structure of the cell of the invention; and FIG. 4 is an electrical schematic view of a typical circuit for operating the polarographic cell module of this invention.

DESCRIPTION OF THE PREFERRED EMBODIMENTS

Referring now to FIGS. 1, 2 and 3, the disposable cell module 10 generally includes a cylindrical housing 12 having an open end 14 over which is mounted a gas permeable membrane 16 secured to the housing by means of a cap 18. A very porous hydrophobic membrane or coating 19 is applied to the outside surface of the gas permeable membrane 16 to prevent interference by water condensation from the atmosphere being tested. The membrane 19 is very thin and porous and has no significant diffusion constant and thus does not interfere with diffusion of oxygen from the atmosphere being tested through the membrane 16 into the underlying electrolyte film. The outside ends 21 of the annular cap extend slightly above the central high point 23 of the membrane, so as to act as a support to prevent damage to either of the membranes 16, 19. The housing and cap are preferably formed of an impermeable material such as a high impact plastic.

A cylindrical cathode support assembly 20 is mounted within the housing forming an annular chamber 22 in the housing 12 for receiving a charge of electrolyte 24. The cathode support assembly 20 is formed of a cylindrical support number 26 having a central bore 28 extending throughout its length. The bore is a lower flared end 30 for receiving the upper end 32 of the cathode pin 34. The upper end of the support member is provided with a recessed cup 35 of larger diameter than the bore which is joined to the bore 28 by a narrow neck portion 36. Cathode 38 is mounted at the outer end of the recessed cup 35 and is connected to a conductor wire 40 which extends through the bore 28 into press fitting engagement with the upper end 32 of the cathode pin 34. The recessed cup 35 and narrow neck portion 36 are filled with sealing compound 39.

The cathode support assembly 20 is formed of an electrolyte resistant insulator. The length of the cathode support member 26 is slightly longer than the inner length of the housing 12 such that the membrane 16 is tightly stretched over the arcuate, curved outer face of the potted cathode 38. The outer corners 41 of the support member 26 are rounded to prevent damage to the membrane 16. The membrane 16 is in contact with the outer curved face of the potting compound filled recessed cup 35 and is evenly separated from the outer edge thereof to provide an even electrolyte film 78 over the exposed cathode points 79. The cathode 38 is in the form of a bent metal wire having a plurality of arms extending radially and then upwardly. The radius of the arms 83 is about the same as the radius of cylindrical cup 35 so that the upper arms 81 are in contact with the outer periphery of the recessed cup 35 so as to be as close as possible to the outside edge thereof. This configuration of disposing the cathode at the periphery of the cup provides lower ion mobility which is important in the low voltage sensing mode contemplated herein.

The cathode 38 may be fabricated by soldering a cross wire 83 to a straight wire 85 at a position downward from the end of the straight wire 85 which is one half the length of the cross wire 83. The cross wire is then bent into the L shaped configuration as is the upper portion of the straignt wire 85 and the L shaped arms are then equally radially disposed 120 degrees apart to form the trident cathode configuration 38 shown in FIG. 3. The lower end of wire 85 is then pulled through the bore 28 until the cathode 38 seats in the recessed cup 35. Potting compound 39 is poured into the recessed cup 35 until it fills the recess and flows partially into the narrow neck portion 36. After the potting compound is cured, a curved slice is removed from the top of the cylindrical reach support member 26 to expose a convex surface and the three cylindrical edges 79 of the catrode assembly 38.

The cathode pin 34 is then inserted through the inner aperture 44 in the bottom wall 46 of the housing 20 until the stop 48 engages the bottom wall 46 and the knurled portion 47 engages the walls of aperture 44. The cathode support assembly is then inserted over upper end 32 of the pin 34 such that the wire 40 is in contact 49 with the pin in 32 and the excess wire 45 is bent upwardly. An anode pin 60 is then similarly inserted through the aperture 62 until the upper pin end 64 is disposed within the electrolyte chamber 22. Potting compound 90 is then poured into the lower end of the housing 12 to seal and electrically insulate the pins 34, 60 from each other and from the electrolyte. The upper end 64 of the pin is maintained exposed to the chamber 22 after the potting operation.

The chamber 22 is then filled with electrolyte 24 and the membrane 16 is then stretched over the opening in the housing 12 over the outer face of the support member 26 and over the O-ring 70 mounted in the groove 71 in the side of the housing 12. The hydrophobic membrane 19 is then applied over the membrane 16 and the cap 18 is then forced over both membranes. Excess membrane is cut off and the O-ring 72 inserted into the groove 74. The module 10 can now be inserted into probe body 76 which will form a liquid tight seal with O-ring 72. The probe 76 has female connectors in the bottom wall thereof for engaging the electrode pins 34, 60 and includes a flexible cord connecting the cell module to the power supply and recording instrument, not shown.

The anode is a non-polarizable metal such as silver. The anode pin may be coated with the metal, have a piece of metal welded or soldered to the pin or the pin can be connected to an annular plug or screen of metal placed in the lower end of the housing.

The anode should have a very high effective area, substantially greater than the cathode. The preferred configuration is the use of a silver mesh or screen 95 soldered to the anode pin end 64. The electrolyte is usually a neutral aqueous salt such as 0.5M, NaCl or KCl.

The electrolyte fills the chamber and flows by capillary action between the gas permeable, electrolyte impermeable plastic membrane and the face of the cathode. Since only a thin film of electrolyte is provided in the sensor and since the majority of the cathode is disposed at the edge, ion mobility is high and tailing type of responses are eliminated. The membrane may be formed from polyethylene or a halohydrocarbon resin such as polytetrafluoroethylene. As oxygen diffuses through the membrane into the electrolyte film thereunder, a current is generated in proportion to the amount of oxygen in the surrounding gas mixture being analyzed. The silver anode undergoes a proportional reaction and the silver is oxidized and silver ions enter the electrolyte and immediately combine with the chloride ions to form silver chloride. The current is sensed in the external circuit and displayed and/or recorded.

The sensitivity and response are high and the oxygen sensing cell provides results with high precision and accuracy with excellent linearity through the range being tested. The anode and electrolyte survive long periods of life sufficient to justify disposal of the sealed module.

The polarographic reducing potentials in aqueous electrolyte are as follows:

TABLE

| Material | Potential, Volts | Threshold |
|---|---|---|
| | Linear Output (minimum) | |
| $O_2$ | −0.55 | −0.20 |
| $N_2O$ | −1.1 | −0.70 |
| $H_2O$ | | −1.25 |

Prior art instruments were operated at −0.7 to −0.9 volts so that both $O_2$ and $N_2O$ were reduced. The cell is operated in accordance with the invention at a preset voltage from −0.55 to −0.70 volts, preferably at about −0.60 volts. The cell may reduce a very small amount of $N_2O$ which is compensated by the electronics of the sensing and recording circuit. Furthermore, at such low voltages, silver cathodes appear to become passivated apparently by reacting with electrolyte, requiring activation at turn-on. The problem is less pronounced with gold or platinum. The invention also includes means to activate the cathode preferably in the form of polarity switching means connected to the cathode. As long as the cathode remains polarized, no passivation occurs.

Referring now to FIG. 4, the sensing and recording circuit generally includes an operational amplifier 100, the output of which is connected to a diode 102 which prevents negative signals from reaching the meter 104. The pin terminal 2 is connected to first and second field effect transistors (FET's) 106, 108. When power is first turned on by closing switch 110, with capacitor 112 discharged, the upper FET 108 is conductive so there is no cutoff bias at gate 114. Capacitor 112 charges and finally provides a bias at gate 114 which cuts off upper FET. The RC time constant is adjusted to cutoff after 10 seconds. When upper FET is conducting, potential from power source 116 applied across electrodes 118, 120 is about 1.2 volts. The lower FET 106 conducts normally and acts as a constant current source and is biased to provide the desired −0.6 volts between contacts 1 and 2 to operate the cell module absent interference from $N_2O$.

The polarographic cell of the invention will also find use in inhallation therapy, neo-natal, geriatric and intensive care for sensing oxygen content or enriched or normal clinical oxygen containing gases.

The invention is able to utilize such small voltage due to low internal electrochemical resistance of the cell. Moving the cathode to the edge of the support also reduces tailing and non-linearity. The cell module of the invention is also less sensitive to pressure fluctuations due to the annular electrolyte body directly exposed to unsupported lower face of the membrane which equally flexes without distortion or lifting. This aspect of the cell module is disclosed and claimed in my copending application, Ser. No. 653,018, now abandoned.

It is to be realized that only preferred embodiments of the invention have been described and that numerous substitutions, alterations and modifications may be made without departing from the spirit and scope of the invention as defined in the following claims.

What is claimed is:

1. A polarographic, electrochemical cell instrument for determining the concentration of a selected gas in a mixture of gases;
    a polarographic cell having a thin electrolyte film disposed between a first cathode electrode formed of a noble metal capable of polarographically reducing oxygen and a gas permeable membrane and having a second, non-polarizable metal, anode electrode in electrical connection with the electrolyte, the combination therewith:
    biasing means for applying a low controlled voltage bias at first polarity between said first and second electrodes at a polarographic reducing potential of the selected gas and below the reducing potential of other gases in the mixture;
    manual, one-way turn-on switching means connected to the biasing means through activation means; and
    activation means for automatically, at turn-on, applying a voltage pulse of second polarity to the first electrode and including electronic timing and cutoff means for terminating said pulse after about ten seconds from turn-on.

2. An instrument according to claim 1 in which the timing means includes a capacitor and means connecting the output side of the capacitor to the gate of a normally non-conducting field effect transistor.

3. An instrument according to claim 1 in which the biasing means includes a normally conducting field effect transistor.

4. An instrument according to claim 1 in which the first electrode includes:
    housing means having an electrode receiving recess provided at one open end thereof defining an electrode face, at least one electrode element disposed in said recess the outer edge of which terminates at the electrode face and the majority of the outer edge surface thereof being nearer to the periphery than to the center of the recess;
    means supporting the element within the recess; and
    means extending through said housing affording electrical connection to the element.

5. An instrument according to claim 4 in which the support means comprises cured potting compound filling said recess and encapsulating the element except for the edge thereof which is exposed at the electrode face.

6. An instrument according to claim 5 in which the ratio of outer exposed electrode element area near the perimeter to exposed inner electrode area near the center is greater than 2.0.

7. An instrument according to claim 6 in which the electrode element is in the form of a plurality of metal wires having exposed first end edges disposed near said periphery and having second ends connected to the electrical connection means.

8. An instrument according to claim 7 in which the first electrode is formed of silver, gold or platinum.

9. An instrument according to claim 8 in which the first and second electrodes are formed of silver.

10. An instrument according to claim 1 in which the selected gas is oxygen, the other gas is nitrous oxide, the low controlled voltage bias is between −0.55 to −0.7 volts and the positive polarity pulse is at least +1.0 volt.

* * * * *